(12) United States Patent
Cranor et al.

(10) Patent No.: US 10,472,565 B2
(45) Date of Patent: Nov. 12, 2019

(54) LOW TEMPERATURE ACTIVATOR SYSTEMS AND METHODS FOR CHEMILUMINESCENT REACTIONS

(71) Applicant: Cyalume Technologies, West Springfield, MA (US)

(72) Inventors: Earl Cranor, Longmeadow, MA (US); Linda Jacob, Woodbridge, CT (US); Patrick Taylor, Holyoke, MA (US)

(73) Assignee: Cyalume Technologies, Inc., West Springfield, MA (US)

( * ) Notice: Subject to any disclaimer, the term of this patent is extended or adjusted under 35 U.S.C. 154(b) by 347 days.

(21) Appl. No.: 14/294,031

(22) Filed: Jun. 2, 2014

(65) Prior Publication Data

US 2014/0356975 A1    Dec. 4, 2014

Related U.S. Application Data

(60) Provisional application No. 61/830,075, filed on Jun. 1, 2013, provisional application No. 61/830,071, filed
(Continued)

(51) Int. Cl.
 *C09K 11/07* (2006.01)
 *C09K 11/02* (2006.01)
 *G01N 21/76* (2006.01)

(52) U.S. Cl.
 CPC ........... *C09K 11/07* (2013.01); *C09K 11/025* (2013.01); *G01N 21/76* (2013.01); *C09K 2211/1007* (2013.01); *C09K 2211/1018* (2013.01)

(58) Field of Classification Search
 CPC .............. C09K 11/07; C09K 11/025; C09K 2211/1018; C09K 11/06; F21K 2/06;
(Continued)

(56) References Cited

U.S. PATENT DOCUMENTS 4,626,383 A * 12/1986 Richter .................. C09K 11/07
                                                    252/700
2012/0097063 A1    4/2012 Cranor et al.
(Continued)

OTHER PUBLICATIONS

"Properties of Organic Solvents", http://murov.info/orgsolvents.htm, Jul. 26, 2012, p. 1-10.*
(Continued)

*Primary Examiner* — Xiaoyun R Xu
(74) *Attorney, Agent, or Firm* — Greenberg Traurig, LLP

(57) ABSTRACT

In some embodiments, the instant invention provides a chemiluminescent system, including: an activator system, including: (a) at least one first solvent, (b) at least one peroxide, (c) at least one catalyst, (d) at least one second solvent, where the at least one second solvent is selected from the group consisting of: tert-butanol, 3-methyl-3-pentanol, 2-methyl-2-butanol, ethyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, propylene glycol dimethyl ether, and a combination thereof; where a combination of the at least one first solvent and the at least one second solvent is present in a sufficient amount in the chemiluminescent system so as to result in the chemiluminescent system producing a light having an illuminescence between 0.1 1x and 35,000 1x at a temperature ranging from −110 degrees Celsius to 75 degrees Celsius.

4 Claims, 1 Drawing Sheet

Related U.S. Application Data on Jun. 1, 2013, provisional application No. 61/830,072, filed on Jun. 1, 2013, provisional application No. 61/830,070, filed on Jun. 1, 2013.

(58) Field of Classification Search
CPC ....... C07C 407/00; C07C 39/08; C07C 69/90; G01N 21/76; G01N 33/533; G01N 2021/7786; G01N 21/643; G01N 33/582; Y10T 436/206664

See application file for complete search history.

(56) References Cited

U.S. PATENT DOCUMENTS

| | | |
|---|---|---|
| 2012/0126188 A1 | 5/2012 | Schrimmer |
| 2014/0353558 A1 | 12/2014 | Cranor et al. |
| 2014/0353559 A1 | 12/2014 | Cranor et al. |
| 2014/0353560 A1 | 12/2014 | Cranor et al. |

OTHER PUBLICATIONS

"tert-Butyl Alcohol", 1991, http://scorecard.goodguide.com/chemical-profiles/html/terbutyl_alcohol.html, 1991, p. 1.*
"2-Methyl-2-Butanol", Mar. 26, 2005, https://pubchem.ncbi.nlm.nih.gov/compound/2-methyl-2-butanol, Mar. 26, 2005, p. 1.*
"Butyl benzoate", http://www.chemicalbook.com/ChemicalProductProperty_EN_cb9357923.htm, 2016, p. 1.*
International Search Report and Written Opinion from International Application No. PCT/US2014/040573 dated Oct. 15, 2014.

\* cited by examiner

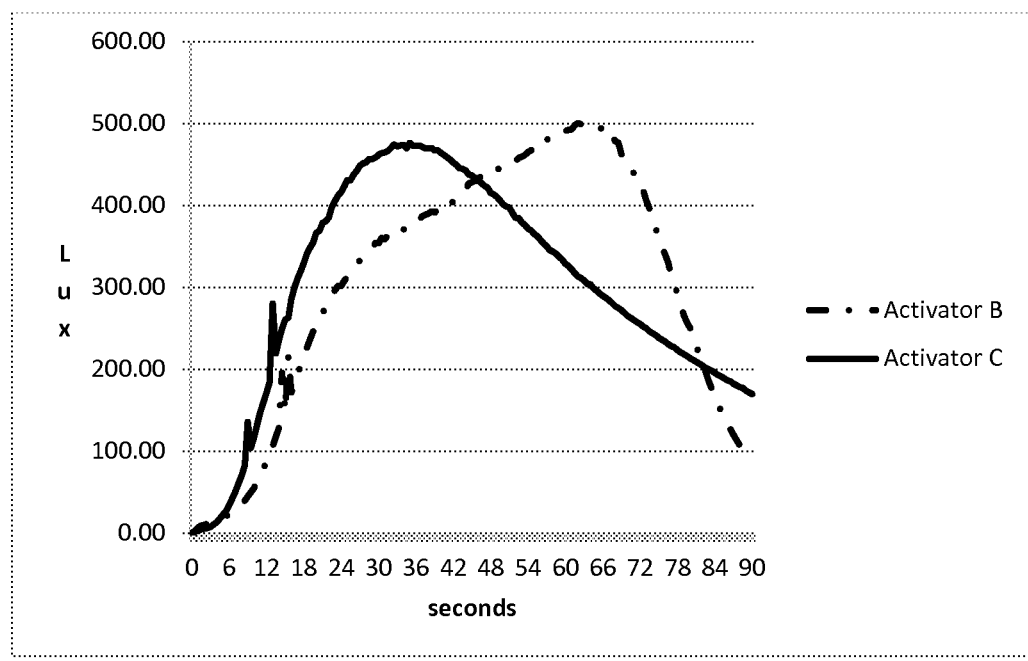

LOW TEMPERATURE ACTIVATOR SYSTEMS AND METHODS FOR CHEMILUMINESCENT REACTIONS

RELATED APPLICATIONS

This application claims the priority of U.S. provisional applications Ser. No. 61/830,070, filed Jun. 1, 2013, entitled "BROAD TEMPERATURE PERFORMANCE CHEMILUMINESCENT SYSTEMS AND METHODS", Ser. No. 61/830,071, filed Jun. 1, 2013, entitled "LOW TEMPERATURE OXALATE SYSTEMS AND METHODS FOR CHEMILUMINESCENT REACTIONS", Ser. No. 61/830,072, filed Jun. 1, 2013, entitled "LOW TEMPERATURE ACTIVATOR SYSTEMS AND METHODS FOR CHEMILUMINESCENT REACTIONS", and Ser. No. 61/830,075, filed Jun. 1, 2013, entitled "MIXED CATALYST SYSTEMS AND METHODS FOR CHEMILUMINESCENT REACTIONS," which are incorporated herein by reference in their entireties for all purposes.

TECHNICAL FIELD

In some embodiments, the present invention relates to chemiluminescent systems and methods.

BACKGROUND

Chemiluminescence is the emission of light as a result of a chemical reaction. There may also be limited emission of heat during the chemical reaction. Typically, a reaction beginning with reactants A and B, with an excited intermediate, yields products and light. Typically, there are many applications that use chemiluminescence. For example, chemiluminescence is used in gas analysis, analysis of inorganic and/or organic species, detection and assay of biomolecules, DNA sequencing, lighting objects, and children's toys.

BRIEF SUMMARY OF INVENTION

In some embodiments, the instant invention provides a chemiluminescent system, including: an activator system, including: (a) at least one first solvent, where the at least one first solvent is selected from the group consisting of: trialkyl citrates, dialkyl phthalates, glycols, glycol ethers, and a combination thereof, (b) at least one peroxide, (c) at least one catalyst, (d) at least one second solvent, where the at least one second solvent is selected from the group consisting of: tert-butanol, 3-methyl-3-pentanol, 2-methyl-2-butanol, ethyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, propylene glycol dimethyl ether, and a combination thereof; where the at least one first solvent is present in a first amount ranging from 15 and 95 percent by weight based on a total weight of the activator system; where the at least one second solvent is present in a second amount ranging from 5 and 85 percent by weight based on the total weight of the activator system; and where a combination of the at least one first solvent and the at least one second solvent is present in a sufficient amount in the chemiluminescent system so as to result in the chemiluminescent system, at a temperature ranging from −110 degrees Celsius to 75 degrees Celsius, producing a light having an illuminescence between 0.1 1× and 35,000 1×.

In some embodiments, the at least one peroxide is present in an amount ranging from 0.25 to 25 percent by weight based on the total weight of the chemiluminescent system.

In some embodiments, the at least one peroxide is selected from the group consisting of: hydrogen peroxide, sodium peroxide, sodium perborate, sodium pyrophosphate peroxide, urea peroxide, histidine peroxide, t-butylhydroperoxide, peroxynehzoic acid, and sodium percarbonate.

In some embodiments, the at least one catalyst is present in a fourth amount ranging from 5 to 0.0005 percent by weight based on the total weight of the chemiluminescent system.

In some embodiments, the chemiluminescent system of claim 1, the at least one catalyst is selected from the group consisting of: dimethylbenzylamine, N,N-dimethyl-1-phenylethylamine, N-ethyl-N-methylbenzyl amine, diethylbenzylamine, N-methyl-N-propylbenzylamine, N,N-dibutylbenzylamine, N,N-bis(1-methylethyl)benzenemethanamine, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, hexyl dibenzylamine, tribenzyl amine, 4-methyl-N,N-bis[(4-methylphenyl)methyl]benzenemethanamine, 4-methyl-N,N-bis(phenylmethyl)benzenemethanamine, N-methyl-N-phenylbenzenemethanamine, N-ethyl-N-phenylbenzenemethanamine, N,4-dimethyl-N-phenylbenzenemethanamine, N-propyl-N-phenylbenzenemethanamine, N,N-diphenylbenzenemethanamine, N,N-bis(4-methylphenyl)benzenemethanamine, lithium benzoate, sodium benzoate, potassium benzoate, cesium benzoate, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and cesium p-anisate.

In some embodiments, the instant invention provides chemiluminescent system, providing: an activator system, including: (a) a solvent, (b) at least one peroxide, (c) at least one catalyst, where the solvent is present in an amount ranging from 5 and 85 percent by weight based on a total weight of the activator system, and where the solvent is configured to be present in a liquidus state at a temperature between −110 degrees Celsius to 75 degrees Celsius.

BRIEF DESCRIPTION OF THE DRAWINGS

The present invention will be further explained with reference to the attached FIGURES. The FIGURES constitute a part of this specification and include illustrative embodiments of the present invention and illustrate various objects and features thereof. The FIGURES shown are not necessarily to scale, with emphasis instead generally being placed upon illustrating the principles of the present invention. Further, some features may be exaggerated to show details of particular components.

FIG. 1 illustrates aspects of some embodiments of the instant invention.

Further, the FIGURES are not necessarily to scale, some features may be exaggerated to show details of particular components. In addition, any measurements, specifications and the like shown in the FIGURES are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

Among those benefits and improvements that have been disclosed, other objects and advantages of this invention will become apparent from the following description taken in conjunction with the accompanying FIGURES. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

"Activation" and variations thereof, as used herein, means that the activation system of the present invention and a suitable oxalate system comprised of an oxalate solution containing one or more suitable oxalate esters with one or more dyes in a suitable solvent with or without other components known to one skilled in the art have been sufficiently combined such as by mixing to provide useable light in a short period such as less than a minute at low temperatures such as down –110 degrees C.

In some embodiments, the present invention relates to an activator system for a chemiluminescent reaction for production of useable light in a short period such as less than a minute at low temperatures down to –110 degrees C. In some embodiments, the activator system can be used in military and non-military training, emergency, and situations where potential ignition sources are hazardous when combined with a suitable oxalate system.

Tracers are employed that allow an observer to visually trace a projectile's trajectory, such as after the firing of munitions in training or combat situations. Winter and high altitude conditions can greatly diminish the effectiveness of current chemiluminescent markers.

In some embodiments, the present invention is an activator system for a chemiluminescent system, where the activator system includes at least one peroxide, at least one catalyst, at least one first solvent, and at least one second solvent configured to allow sufficient mixing of the at least one peroxide, and where, when the activator system is mixed with an oxalate system for the chemiluminescent system, the chemiluminescent system is configured to provide light at a temperature of –110 degrees C.

In some embodiments, the at least one peroxide is selected from the group consisting of hydrogen peroxide; sodium peroxide; sodium perborate; sodium pyrophosphate peroxide; urea peroxide; histidine peroxide; t-butylhydroperoxide; peroxybenzoic acid, and sodium percarbonate.

In some embodiments, the at least one peroxide is present in an amount ranging from 0.25 percent to 25 percent by weight, based on the total weight of the combined activator system and oxalate system.

In some embodiments, the at least one first solvent is selected from the group consisting of trialkyl citrates, dialkyl phthalates, glycols, and glycol ethers.

In some embodiments, the at least one catalyst is selected from the group consisting of dimethylbenzylamine, N,N-dimethyl-1-phenylethylamine, N-ethyl-N-methylbenzylamine, diethylbenzylamine, N-methyl-N-propylbenzylamine, N,N-dibutylbenzylamine, N,N-bis(1-methylethyl)benzenemethanamine, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, hexyl dibenzylamine, tribenzyl amine, 4-methyl-N,N-bis[(4-methylphenyl)methyl]benzenemethanamine, 4-methyl-N,N-bis(phenylmethyl)benzenemethanamine, N-methyl-N-phenylbenzenemethanamine, N-ethyl-N-phenylbenzenemethanamine, N,4-dimethyl-N-phenylbenzenemethanamine, N-propyl-N-phenylbenzenemethanamine, N,N-diphenylbenzenemethanamine, N,N-bis(4-methylphenyl)benzenemethanamine, lithium benzoate, sodium benzoate, potassium benzoate, cesium benzoate, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and cesium p-anisate.

In some embodiments, the at least one catalyst is present in a concentration ranging from 5 percent to 0.0005 percent of the total weight of the combined activator system and oxalate system.

In some embodiments, the activator system includes a second solvent configured to dissolve the at least one catalyst and allow mixing of the at least one peroxide, wherein the second solvent is selected from the group consisting of aliphatic tertiary alcohols, chosen from, but not restricted to, tert-butanol, 3-methyl-3-pentanol, 2-methyl-2-butanol, ethyl 2-hydroxyisobutyrate, alkyl 2-hydroxyisobutyrates, and methyl 2-hydroxyisobutyrate; glycols; ethylene glycol and propylene glycol; glycol ethers; ethylene glycol monomethyl ether, ethylene glycol diethyl ether, ethylene glycol monobutyl ether, ethylene glycol dibutyl ether, and propylene glycol dimethyl ether.

In some embodiments, the at least second solvent is present in a concentration ranging from 0 percent to 90 percent of the total weigh to activator system.

In some embodiments, the activator system, when combined with a suitable oxalate system, provides a chemiluminescent activator system that performs at low temperatures to provide usable light.

In some embodiments, the activator system, when combined with a suitable oxalate system, emits light. In some embodiments, the activator system includes at least one peroxide, at least one catalyst, at least one bridging solvent (i.e., "second solvent") to assist with the solubility of the peroxide component if necessary, and at least one solvent that has a sufficiently low melting point and is compatible with the chemical reactions required to produce chemiluminesence.

In some embodiments, the activator system of the present invention produces useable light at low temperatures when activated.

In some embodiments, the oxalate system may include, but is not limited to, at least one oxalate ester, at least one dye such as a fluorescer, at least one inorganic salt, wherein the at least one inorganic salt is chosen from sodium thiosulphate, potassium thiosulphate, cobalt acetate, copper acetate, lead acetate, cupric chloride, ferric chloride, calcium iodide, potassium iodide, and silver nitrate, and at least one low boiling solvent chosen from, but not restricted to, alkyl benzoates, dialkyl malonates, dialkyl dialkylmalonates, dialkyl arylalkylmalonates, dialkyl succinates, dialkyl glutarates, dialkyl adipates, dialkyl pimelates, dialkyl polyalkylmalonates, acetyl trialkyl citrates, 2-acetyloxy isobutyrates, paraffinic liquids, isoparaffinic liquids, toluene, nitroethane, or a mixture of any of the above.

In some embodiments, the ratio of the weight of the oxalate system to the weight of the activator system ranges from 1:9 to 4:1. In some embodiments, the ratio of the weight of the oxalate system to the weight of the activator system ranges from 1:5 to 2:1. In some embodiments, the ratio of the weight of the oxalate system to the weight of the activator system ranges from 1:1 to 3:1. In some embodiments, the ratio of the weight of the oxalate system to the weight of the activator system ranges from 1:3 to 3:1. In some embodiments, the ratio of the weight of the oxalate system to the weight of the activator system ranges from 1:2 to 2:1. In some embodiments, the ratio of the weight of the oxalate system to the weight of the activator system ranges from 2:1 to 4:1. In some embodiments, the ratio of the weight of the oxalate system to the weight of the activator system ranges from 1:6 to 2:1. In some embodiments, the ratio of the weight of the oxalate system to the weight of the activator system ranges from 1:1 to 4:1.

In some embodiments, the ratio of the weight of the oxalate system to the weight of the activator system is 1:2. In some embodiments, the ratio of the weight of the oxalate system to the weight of the activator system is 2:1. In some embodiments, the ratio of the weight of the oxalate system to the weight of the activator system is 3:1. In some embodiments, the ratio of the weight of the oxalate system to the weight of the activator system is 1:8. In some embodiments, the ratio of the weight of the oxalate system to the weight of the activator system is 8:2. In some embodiments, the ratio of the weight of the oxalate system to the weight of the activator system is 4:1. In some embodiments, the ratio of the weight of the oxalate system to the weight of the activator system is 1:9. In some embodiments, the ratio of the weight of the oxalate system to the weight of the activator system is 1:5. In some embodiments, the ratio of the weight of the oxalate system to the weight of the activator system is 1:3.

In some embodiments, the system of the present invention, when activated, is configured to produce useable light in a temperature range of −110° C. to 75° C. In some embodiments, the system of the present invention, when activated, is configured to produce useable light in a temperature range of −80° C. to 50° C. In some embodiments, the system of the present invention, when activated, is configured to produce useable light in a temperature range of −110° C. to 50° C. In some embodiments, the system of the present invention, when activated, is configured to produce useable light in a temperature range of −80° C. to 75° C. In some embodiments, the system of the present invention, when activated, is configured to produce useable light in a temperature range of −30° C. to 30° C. In some embodiments, the system of the present invention, when activated, is configured to produce useable light in a temperature range of −100° C. to 0° C. In some embodiments, the system of the present invention, when activated, is configured to produce useable light in a temperature range of −20° C. to 75° C. In some embodiments, the system of the present invention, when activated, is configured to produce useable light in a temperature down to −110° C. In some embodiments, the system of the present invention, when activated, is configured to produce useable light in a temperature range of −60° C. to 20° C. In some embodiments, the system of the present invention, when activated, is configured to produce useable light in a temperature range of −110° C. to −10° C.

In some embodiments, the system of the present invention, when activated, is configured to produce useable light for a duration of 1 second to 3 minutes. In some embodiments, the system of the present invention, when activated, is configured to produce useable light for a duration of 10 seconds to 3 minutes. In some embodiments, the system of the present invention, when activated, is configured to produce useable light for a duration of 1 second to 2 minutes. In some embodiments, the system of the present invention, when activated, is configured to produce useable light for a duration of 30 seconds to 1 minute. In some embodiments, the system of the present invention, when activated, is configured to produce useable light for a duration of 20 seconds to 2 minute. In some embodiments, the system of the present invention, when activated, is configured to produce useable light for a duration of 2 minutes to 3 minutes. In some embodiments, the system of the present invention, when activated, is configured to produce useable light for a duration of 1 minute to 2 minutes.

In some embodiments, the system of the present invention, when activated, is configured to produce useable light for a duration of 10 seconds. In some embodiments, the system of the present invention, when activated, is configured to produce useable light for a duration of 1 minute. In some embodiments, the system of the present invention, when activated, is configured to produce useable light for a duration of 30 seconds. In some embodiments, the system of the present invention, when activated, is configured to produce useable light for a duration of 2 minutes. In some embodiments, the system of the present invention, when activated, is configured to produce useable light for a duration of 15 seconds. In some embodiments, the system of the present invention, when activated, is configured to produce useable light for a duration of 1.5 minutes. In some embodiments, the system of the present invention, when activated, is configured to produce useable light for a duration of 45 seconds.

In some embodiments, the activator system for a chemiluminescent reaction system is comprised of at least one peroxide, at least one catalyst, at least one low melting point solvent and at least one bridging solvent, if required, to allow sufficient mixing of the peroxide component.

In some embodiments the at least one peroxide may include, but is not limited to, hydrogen peroxide; sodium peroxide; sodium perborate; sodium pyrophosphate peroxide; urea peroxide; histidine peroxide; t-butylhydroperoxide; peroxybenzoic acid, and/or sodium percarbonate.

In some embodiments, the at least one peroxide is present in an amount ranging from 0.25 percent to 25 percent by weight, based on the total weight of the combined activator system and oxalate system. In some embodiments, the at least one peroxide is present in an amount ranging from 5 percent to 25 percent by weight, based on the total weight of the combined activator system and oxalate system. In some embodiments, the at least one peroxide is present in an amount ranging from 1 percent to 20 percent by weight, based on the total weight of the combined activator system and oxalate system. In some embodiments, the at least one peroxide is present in an amount ranging from 10 percent to 15 percent by weight, based on the total weight of the combined activator system and oxalate system. In some embodiments, the at least one peroxide is present in an amount ranging from 0.25 percent to 5 percent by weight, based on the total weight of the combined activator system and oxalate system.

In some embodiments, the at least one peroxide is present at 0.25 percent by weight, based on the total weight of the combined activator system and oxalate system. In some embodiments, the at least one peroxide is present at 1 percent by weight, based on the total weight of the combined activator system and oxalate system. In some embodiments, the at least one peroxide is present at 5 percent by weight, based on the total weight of the combined activator system and oxalate system. In some embodiments, the at least one peroxide is present at 10 percent by weight, based on the total weight of the combined activator system and oxalate system. In some embodiments, the at least one peroxide is present at 20 percent by weight, based on the total weight of the combined activator system and oxalate system. In some embodiments, the at least one peroxide is present at 25 percent by weight, based on the total weight of the combined activator system and oxalate system.

In some embodiments, the at least one peroxide is present at the weight percents and the weight percent ranges detailed above, based on the weight of the activator system.

In some embodiments, the at least one low melting point solvent (i.e., "first solvent") may include, but is not limited to, trialkyl citrates, dialkyl phthalates, glycols, glycol ethers and any combination thereof.

In some embodiments, the at least one first solvent is present in an amount ranging from 0 percent to 95 percent of the total weight of the activator system. In some embodiments, the at least one first solvent is present in an amount ranging from 10 percent to 97 percent of the total weight of the activator system. In some embodiments, the at least one first solvent is present in an amount ranging from 10 percent to 80 percent of the total weight of the activator system. In some embodiments, the at least one first solvent is present in an amount ranging from 10 percent to 60 percent of the total weight of the activator system. In some embodiments, the at least one first solvent is present in an amount ranging from 30 percent to 90 percent of the total weight of the activator system. In some embodiments, the at least one first solvent is present in an amount ranging from 15 percent to 90 percent of the total weight of the activator system. In some embodiments, the at least one first solvent is present in an amount ranging from 50 percent to 95 percent of the total weight of the activator system. In some embodiments, the at least one first solvent is present in an amount ranging from 0 percent to 10 percent of the total weight of the activator system.

In some embodiments, the at least one first solvent is present at 0 percent of the total weight of the activator system. In some embodiments, the at least one first solvent is present at 20 percent of the total weight of the activator system. In some embodiments, the at least one first solvent is present at 40 percent of the total weight of the activator system. In some embodiments, the at least one first solvent is present at 60 percent of the total weight of the activator system. In some embodiments, the at least one first solvent is present at 95 percent of the total weight of the activator system. In some embodiments, the at least one first solvent is present at 97 percent of the total weight of the activator system.

In some embodiments, the at least one catalyst may include, but is not limited to, dimethylbenzyl amine, N,N-dimethyl-1-phenylethylamine, N-ethyl-N-methylbenzylamine, diethylbenzylamine, N-methyl-N-propylbenzylamine, N,N-dibutylbenzylamine, N,N-bis(1-methylethyl)benzenemethanamine, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, hexyl dibenzylamine, tribenzyl amine, 4-methyl-N,N-bis[(4-methylphenyl)methyl]benzenemethanamine, 4-methyl-N,N-bis(phenylmethyl)benzenemethanamine, N-methyl-N-phenylbenzenemethanamine, N-ethyl-N-phenylbenzenemethanamine, N,4-dimethyl-N-phenylbenzenemethanamine, N-propyl-N-phenylbenzenemethanamine, N,N-diphenylbenzenemethanamine, N,N-bis(4-methylphenyl)benzenemethanamine, lithium benzoate, sodium benzoate, potassium benzoate, cesium benzoate, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and/or cesium p-anisate.

In some embodiments, the at least one catalyst is present at a concentration ranging from 5% to 0.0005% by weight, based on the total weight of the combined activator system and oxalate system. In some embodiments, the at least one catalyst is present at a concentration ranging from 2% to 0.1% by weight, based on the total weight of the combined activator system and oxalate system. In some embodiments, the at least one catalyst is present at a concentration ranging from 1% to 0.0005% by weight, based on the total weight of the combined activator system and oxalate system. In some embodiments, the at least one catalyst is present at a concentration ranging from 5% to 2% by weight, based on the total weight of the combined activator system and oxalate system. In some embodiments, the at least one catalyst is present at a concentration ranging from 0.7% to 0.0005% by weight, based on the total weight of the combined activator system and oxalate system. In some embodiments, the at least one catalyst is present at a concentration ranging from 0.5% to 0.05% by weight, based on the total weight of the combined activator system and oxalate system. In some embodiments, the at least one catalyst is present at a concentration ranging from 5% to 3% by weight, based on the total weight of the combined activator system and oxalate system.

In some embodiments, the at least one catalyst is present at 5% by weight, based on the total weight of the combined activator system and oxalate system. In some embodiments, the at least one catalyst is present at 0.5% by weight, based on the total weight of the combined activator system and oxalate system. In some embodiments, the at least one catalyst is present at 0.05% by weight, based on the total weight of the combined activator system and oxalate system. In some embodiments, the at least one catalyst is present at 0.005% by weight, based on the total weight of the combined activator system and oxalate system. In some embodiments, the at least one catalyst is present at 0.0005% by weight, based on the total weight of the combined activator system and oxalate system. In some embodiments, the at least one catalyst is present at 2% by weight, based on the total weight of the combined activator system and oxalate system. In some embodiments, the at least one catalyst is present at 3% by weight, based on the total weight of the combined activator system and oxalate system.

In some embodiments, the at least one catalyst is present at the weight percents and the weight percent ranges detailed above, based on the weight of the activator system.

In some embodiments, the at least one catalyst is dissolved in a suitable solvent wherein the at least one bridging solvent (i.e., second solvent), if necessary to allow sufficient mixing of the peroxide component may include, but is not limited to, tert-butanol, 3-methyl-3-pentanol, 2-methyl-2-butanol, ethyl 2-hydroxyisobutyrate, alkyl 2-hydroxyisobutyrates and methyl 2-hydroxyisobutyrate; glycols chosen from, but not restricted to ethylene glycol and propylene glycol; and glycol ethers chosen from, but not restricted to ethylene glycol monomethyl ether, ethylene glycol diethyl ether, ethylene glycol monobutyl ether, ethylene glycol dibutyl ether, propylene glycol dimethyl ether and any combination thereof. In some embodiments, the at least one second solvent is present in an amount ranging from 0 percent to 95 percent of the total weight of the activator system. In some embodiments, the at least one second solvent is present in an amount ranging from 10 percent to 97 percent of the total weight of the activator system. In some embodiments, the at least one second solvent is present in an amount ranging from 10 percent to 80 percent of the total weight of the activator system. In some embodiments, the at least one second solvent is present in an amount ranging from 10 percent to 60 percent of the total weight of the activator system. In some embodiments, the at least one second solvent is present in an amount ranging from 30 percent to 90 percent of the total weight of the activator system. In some embodiments, the at least one second solvent is present in an amount ranging from 15 percent to 90 percent of the total weight of the activator system. In some embodiments, the at least one second solvent is present in an amount ranging from 50 percent to 95 percent of the total weight of the activator system. In some embodiments, the at least one second solvent is present in an amount ranging from 0 percent to 10 percent of the total weight of the activator system.

In some embodiments, the at least one second solvent is present at 0 percent of the total weight of the activator system. In some embodiments, the at least one second solvent is present at 20 percent of the total weight of the activator system. In some embodiments, the at least one second solvent is present at 40 percent of the total weight of the activator system. In some embodiments, the at least one second solvent is present at 60 percent of the total weight of the activator system. In some embodiments, the at least one second solvent is present at 95 percent of the total weight of the activator system. In some embodiments, the at least one second solvent is present at 97 percent of the total weight of the activator system.

Non-Limiting Example 1

The experiments in Table I indicate that the ratio of the solvents, in this case triethylcitrate (TEC) or tributyl citrate (TBC) and an auxiliary solvent comprising either diethylene glycol diethyl ether (DEGDE) or methyl 2-hydroxybutyrate (MHB), used may be adjusted based, at least in part, on the desired operating temperature. The viscosities were measured using a Brookfield viscometer and the temperature of the solution recorded digitally during the experiment.

TABLE I

| Activator Formula | TEC (g) | TBC (g) | DEDGE (g) | MHB (g) | 50% aq. Hydrogen Peroxide (g) | Sodium Salicylate (g) | Temp (° C.) | Viscosity (cP) |
|---|---|---|---|---|---|---|---|---|
| A | 199.5 | | 250 | | 50 | 0.5 | −31 | 210 |
|   | 199.5 | | 250 | | 50 | 0.5 | −64 | 123,300 |
| B | 149.5 | | | 300 | 50 | 0.5 | −31 | 654 |
|   | 149.5 | | | 300 | 50 | 0.5 | −60 | 127,300 |
| C | | 149.5 | 300 | | 50 | 0.5 | −31 | 180 |
|   | | 149.5 | 300 | | 50 | 0.5 | −63 | 21,320 |

Non-Limiting Example 2

The light output for a variety of activators at low temperatures was measured by reacting the different formulations with an oxalate made from 14% bis(2,4,5-trichloro-6-carbopentoxyphenyl)oxalate (CPPO) and 0.3% rubrene in a solvent comprised of 50% bis(1-methylethyl) malonate and 50% butyl benzoate. The activator solution (1.0 g each) and oxalate solution (0.8 g with 0.1 g of sodium thiosulfate) were sealed in glass ampoules. The sealed ampoules were cooled to −86 degrees C. in a freezer for a minimum of 2 hours. At that point, 2 oxalate and four activator ampoules were placed in the in an ampoule crushing device with a light meter for each test. The tests were conducted measuring the light output with an ILT 1700 light meter. The readings were started within one minute or less after removal from the freezer. The results are shown in FIG. 1. FIG. 1 represents the chemical light output of activator formulas B & C at −86 degrees C.

In some embodiments, the instant invention provides a chemiluminescent system, including: an activator system, including: (a) at least one first solvent, where the at least one first solvent is selected from the group consisting of: trialkyl citrates, dialkyl phthalates, glycols, glycol ethers, and a combination thereof, (b) at least one peroxide, (c) at least one catalyst, (d) at least one second solvent, where the at least one second solvent is selected from the group consisting of: tert-butanol, 3-methyl-3-pentanol, 2-methyl-2-butanol, ethyl 2-hydroxyisobutyrate, methyl 2-hydroxyisobutyrate, ethylene glycol, propylene glycol, ethylene glycol monomethyl ether, ethylene glycol diethyl ether, ethylene glycol monobutyl ether, ethylene glycol dibutyl ether, propylene glycol dimethyl ether, and a combination thereof; where the at least one first solvent is present in a first amount ranging from 15 and 95 percent by weight based on a total weight of the activator system; where the at least one second solvent is present in a second amount ranging from 5 and 85 percent by weight based on the total weight of the activator system; and where a combination of the at least one first solvent and the at least one second solvent is present in a sufficient amount in the chemiluminescent system so as to result in the chemiluminescent system, at a temperature ranging from −110 degrees Celsius to 75 degrees Celsius, producing a light having an illuminescence between 0.1 1× and 35,000 1×.

In some embodiments, the at least one peroxide is present in an amount ranging from 0.25 to 25 percent by weight based on the total weight of the chemiluminescent system.

In some embodiments, the at least one peroxide is selected from the group consisting of: hydrogen peroxide, sodium peroxide, sodium perborate, sodium pyrophosphate peroxide, urea peroxide, histidine peroxide, t-butylhydroperoxide, peroxynehzoic acid, and sodium percarbonate.

In some embodiments, the at least one catalyst is present in a fourth amount ranging from 5 to 0.0005 percent by weight based on the total weight of the chemiluminescent system.

In some embodiments, the chemiluminescent system of claim 1, the at least one catalyst is selected from the group consisting of: dimethylbenzylamine, N,N-dimethyl-1-phenylethylamine, N-ethyl-N-methylbenzylamine, diethylbenzylamine, N-methyl-N-propylbenzylamine, N,N-dibutylbenzylamine, N,N-bis(1-methylethyl)benzenemethanamine, methyl dibenzylamine, ethyl dibenzylamine, n-propyl dibenzylamine, iso-propyl dibenzylamine, butyl dibenzylamine, iso-butyl dibenzylamine, N,N-dibenzyl-2-phenylethanamine, hexyl dibenzylamine, tribenzyl amine, 4-methyl-N,N-bis[(4-methylphenyl)methyl]benzenemethanamine, 4-methyl-N,N-bis(phenylmethyl)benzenemethanamine, N-methyl-N-phenylbenzenemethanamine, N-ethyl-N-phenylbenzenemethanamine, N,4-dimethyl-N-phenylbenzenemethanamine, N-propyl-N-phenylbenzenemethanamine, N,N-diphenylbenzenemethanamine, N,N-bis(4-methylphenyl)benzenemethanamine, lithium benzoate, sodium benzoate, potassium benzoate, cesium benzoate, lithium salicylate, sodium salicylate, potassium salicylate, cesium salicylate, lithium o-anisate, sodium o-anisate, potassium o-anisate, cesium o-anisate, lithium p-anisate, sodium p-anisate, potassium p-anisate, and cesium p-anisate.

In some embodiments, the instant invention provides chemiluminescent system, providing: an activator system, including: (a) a solvent, (b) at least one peroxide, (c) at least one catalyst, where the solvent is present in an amount ranging from 5 and 85 percent by weight based on a total weight of the activator system, and where the solvent is configured to be present in a liquidus state at a temperature between −110 degrees Celsius to 75 degrees Celsius.

While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A chemiluminescent system, comprising:
an activator system, comprising:
(a) at least one first solvent,
wherein the at least one first solvent is selected from the group of: triethyl citrate, ethylene glycol methyl ether, ethylene glycol dibutyl ether, and a combination thereof,
(b) at least one peroxide,
(c) at least one second solvent, wherein,
(i) when the at least one first solvent comprises triethyl citrate, the at least one second solvent is selected from the group of: 2-methyl-2-pentanol, methyl 2-hydroxyisobutyrate, and a combination thereof;
(ii) when the at least one first solvent comprises ethylene glycol methyl ether, the at least one second solvent is methyl 2-hydroxyisobutyrate; and
(iii) when the at least one first solvent comprises ethylene glycol dibutyl ether, the at least one second solvent is 3-methyl-3-pentanol or 2-methyl-2-butanol; and
wherein the at least one first solvent and the at least one second solvent form a solvent mixture configured to be present in a liquid state at a temperature between −110 degrees Celsius to 75 degrees Celsius; and
(d) at least one catalyst,
wherein the at least one catalyst is soluble in the solvent mixture and is selected from the group consisting of: dimethylbenzylamine, N,N-dimethyl-1-phenylethylamine, N-ethyl-N-methylbenzylamine, diethylbenzylamine, N-methyl-N-propylbenzylamine, N,N-dibutylbenzylamine, N,N-bis(1-methylethyl)benzenemethanamine, methyl dibenzylamine, ethyl dibenzylamine, n-propyl dibenzylamine, iso-propyl dibenzylamine, butyl dibenzylamine, isobutyl dibenzylamine, N,N-dibenzyl-2-phenylethanamine, hexyl dibenzylamine, tribenzyl amine, 4-methyl-N,N-bis[(4-methylphenyl)methyl]benzenemethanamine, 4-methyl-N,Nbis(phenylmethyl)benzenemethanamine, N-methyl-N-phenylbenzenemethanamine, N-ethyl-N-phenylbenzenemethanamine, N,4-dimethyl-N-phenylbenzenemethanamine, phenylbenzenemethanamine, N, N-diphenylbenzenemethanamine, N-propyl-NN, N-bis(4-methylphenyl)benzenemethanamine, sodium benzoate, potassium benzoate, cesium benzoate, sodium salicylate, potassium salicylate, cesium salicylate, sodium o-anisate, potassium o-anisate, cesium o-anisate, sodium p-anisate, potassium p-anisate, and cesium p-anisate;
wherein the at least one first solvent is present in a first amount ranging from 25 and 65 percent by weight based on a total weight of the activator system;
wherein the at least one second solvent is present in a second amount ranging from 25 and 65 percent by weight based on the total weight of the activator system;
wherein a combination of the at least one first solvent and the at least one second solvent is present in a sufficient amount in the chemiluminescent system so as to result in the chemiluminescent system producing a light having an illuminescence between 0.1 lux and 35,000 lux.

2. The chemiluminescent system of claim 1, wherein the at least one peroxide is present in a third amount ranging from 0.25 to 25 percent by weight based on the total weight of the chemiluminescent system.

3. The chemiluminescent system of claim 1, wherein the at least one peroxide is selected from the group consisting of: hydrogen peroxide, sodium peroxide, sodium perborate, sodium pyrophosphate peroxide, urea peroxide, histidine peroxide, t-butylhydroperoxide, peroxynehzoic acid, and sodium percarbonate.

4. The chemiluminescent system of claim 1, wherein the at least one catalyst is present in a fourth amount ranging from 5 to 0.0005 percent by weight based on the total weight of the chemiluminescent system.

* * * * *